United States Patent [19]

Smith et al.

[11] Patent Number: 4,826,660
[45] Date of Patent: May 2, 1989

[54] DETECTOR ASSEMBLY FOR ANALYZER INSTRUMENT

[75] Inventors: Roger E. Smith, Bountiful; Randall W. Smith, Sandy, both of Utah

[73] Assignee: Becton, Dickinson and Company, Franklin Lakes, N.J.

[21] Appl. No.: 46,953

[22] Filed: May 7, 1987

[51] Int. Cl.⁴ ............................................. G01N 21/64
[52] U.S. Cl. ...................................... 422/68; 356/246; 356/419; 356/440; 422/64; 422/65
[58] Field of Search ............... 356/244, 246, 418, 419, 356/440; 422/63–67, 68

[56] References Cited

U.S. PATENT DOCUMENTS

| | | | |
|---|---|---|---|
| 2,701,502 | 2/1955 | Lukens et al. | 356/418 |
| 3,975,103 | 8/1976 | Mannucci | 356/419 |
| 4,090,789 | 5/1978 | Macemon et al. | 356/244 |
| 4,090,791 | 5/1978 | Siddiqi et al. | 356/244 |
| 4,213,703 | 7/1980 | Haunold et al. | 356/244 |
| 4,291,230 | 9/1981 | Heiss | 356/244 |
| 4,431,307 | 2/1984 | Suovaniemi | 356/440 |
| 4,586,818 | 5/1986 | Lohr | 356/244 |
| 4,614,434 | 9/1986 | Welch | 356/418 |
| 4,678,752 | 7/1987 | Thorne et al. | 422/65 |
| 4,730,933 | 3/1988 | Lohr | 356/440 |

Primary Examiner—Michael S. Marcus
Attorney, Agent, or Firm—Aaron Passman

[57] ABSTRACT

A detector assembly for use with an analyzer instrument comprises a light source for providing a light beam for analyzing one or more substances in a sample. A detector is included for detecting light associated with the sample under analysis. An analysis station permits the light beam to enter the sample and shields the sample from extraneous light. The analysis station further permits light to pass from the sample to the light detector. A plurality of filters is selectively positionable in the light beam between the light source and the sample. These filters permit different wavelengths of light to pass therethrough so that selective light analysis of the sample may be performed.

21 Claims, 7 Drawing Sheets

DETECTOR ASSEMBLY FOR ANALYZER INSTRUMENT

BACKGROUND OF THE INVENTION

1. Field of the Invention

The present invention relates generally to an analyzer instrument, and more particularly, concerns a detector assembly for use in an instrument for detecting light associated with the chemical, immunochemical or biological testing of samples.

2. Description of the Prior Art

Automatic analyzer instruments are presently used for a variety of chemical, immunochemical and biological tests for substances in samples. The use of radiant energy from a light source, such as a lamp, to establish a basis for the analysis of the samples is quite prevalent in presently known and available automatic analyzers. When a light source is employed in such analyzers, the test liquid may be monitored for a number of light-associated responses including colorimetric, fluorometric, nephelometric or light scatter, absorbance and the like.

In automatic analyzers, particularly those using radiant energy from a light source for analysis purposes, it is desirable to perform a test on many samples in a single run of the equipment. To facilitate the testing of multiple samples, many analyzers use a carousel or a turntable for holding the samples, usually in liquid form, to be analyzed. The sample liquid is typically carried in different kinds of vehicles, including tubes, cuvettes, bags, cups and the like carriers. In an automatic analyzer which employs a carousel or turntable, along with a light source for analysis purposes, some mechanism is generally provided for passing each test sample before the light source so that individual analysis of the test samples may be achieved. Representative instruments of the aforementioned type are described in U.S. Pat. No. 4,483,927 and by DeGrella et al. in "A Nephelometry System for the Abbott TDx ™ Analyzer," Clin. Chem. 31/9, 1474–1477 (1985).

In many instances, the carriers which hold the liquid sample for analysis have circular cross-sections, such as test tubes or cups. These round sample carriers introduce the possibility of inaccuracies in the detection system. Specifically, when the light beam is directed at a rounded surface surrounding the test sample, positional variations in the test tube could result in diminished efficiency of the light signal due to undesirable refraction of the light beam. Of course, positional variations of the carrier of the test sample could occur whether or not the carrier has a rounded cross-section; it is emphasized here that rounded tubes or cups introduce the possibility of magnifying the inaccuracies due to positional variations. Corrections for positional and temporal variations in the test sample carrier may be made by reliance on a reference standard associated with the light signal and by use of a ratio of measured signal and reference signal. One such approach for a corrected result, to eliminate positional and temporal variations, is described in the aforementioned article by DeGrella et al. However, short of using reference signals and ratios, which complicate the instrument and the electrical circuitry therefor, improvements are still being sought in eliminating positional variations of the test sample carrier, from the physical location standpoint, so that inaccuracies of the detection system may be minimized.

In addition to the just-mentioned improvements, it is also desirable, particularly with an automatic analyzer instrument, to be able to conduct the light analysis of the sample at different wavelengths on an automatic basis. For example, during a single run of the multiple test tubes in the instrument, it is frequently desirable to be able to detect different colorimetric or fluorometric responses of the samples. Since interference filters are commonly employed to provide selective wavelength analysis of test samples, many instruments require the changing of these filters, in the middle of a test run, in order to conduct multiple wavelength analysis. Implementation of an automated optical system for providing multiple and selective wavelength analysis would facilitate the efficiency of the analyzer instrument. It is toward the fulfillment of tthe above-described desiderata, and other features particularly relating to optical elements of automated analyzer instruments, that the present invention is directed.

SUMMARY OF THE INVENTION

The detector assembly of the present invention is useful with an analyzer instrument and comprises means for providing a light beam for analyzing one or more substances in a sample. Means are provided for detecting light associated with the sample under analysis. Additional means permits the light beam to enter the sample and also shields the sample from extraneous light. Light is permitted to pass from the sample to the means for detecting. A plurality of filters is selectively positionable in the light beam between the means for providing light and the sample. The filters permit different wavelengths of light to pass therethrough so that selective light analysis of the sample may be performed.

In a preferred embodiment of the invention, the detector assembly includes an analysis station comprising a movable body member with a substantially cylindrical bore into which a tube carrying the sample to be analyzed is positionable. The body member surrounds the tube, when positioned in the bore, to shield the sample from extraneous light. A first aperture in the body member is in communication with the bore for permitting the light beam to enter the tube with the sample. A second aperture is in communication with the bore for permitting light to pass from the sample to the light detector so that the sample may be analyzed. In this embodiment, the body member is operatively movable between a first position at which the bore surrounds the tube and a second position out of surrounding association with the tube to facilitate the passage of the tube into and out of the analysis station. A rotatable filter wheel includes the plurality of light filters, which are removably mounted in the wheel. These filters are spaced in a substantially circular arrangement in the wheel so that each filter is interposable in the light beam between the source of light and the analysis station. Accordingly, the filters permit different wavelengths of light to pass therethrough for the selective light analysis of the sample, depending upon the position of the filter wheel. In this preferred embodiment, means for rotating the wheel are provided so that each filter is selectively positionable in the light beam.

In accordance with the principles of the present invention, a detector assembly is provided which is eminently suitable for use in an instrument for the chemical, immunochemical or biological testing of samples, particularly those samples carried in a light transmissive carrier. While the present invention provides a number of advantages and benefits in the optical arrangement of a light-based detector assembly, including improvements in the efficiency of the analyzer, there are a few significant advantages that are noteworthy. For instance, the present invention provides a feature for employing multiple light filters so that selective light analysis of the test sample may be performed. These filters are preferably removable or interchangeable in a filter wheel arrangement, without the need for disassembling the filter wheel from the detector assembly itself. Further, inasmuch as the filter wheel is rotatable, multiple wavelength analysis may be performed incrementally by the mere rotation of the wheel until a different filter is interposed in the light beam between the light source and the sample under analysis. In the preferred embodiment, a motor is associated with the rotation of the filter wheel so that the wheel may be automatically rotated to the different filter positions.

In one embodiment of the present invention, the analysis station includes an operatively movable body member into which the tube, carrying the test sample, is positionable. This body member not only shields the tube from extraneous light, but serves as a guide for holding the tube in position during the operation of the analyzer. Further, since the position of the body member does not vary with respect to the direction of the light beam, each tube which is placed therein is not positionally different from tube-to-tube. Accordingly, positional variations, which may introduce inaccuracies into the detection system, are not only controlled by the preferred body member of the present invention, but the inaccuracies are minimized or reduced.

It is another feature of the present invention, particularly associated with the operatively movable body member, that tubes carrying test samples may remain in a carousel or turntable during the light analysis steps. In other words, each tube containing the sample for analysis does not have to be removed from the carousel for placement in the analysis station; the preferred detector assembly of the present invention allows the carousel or turntable to incrementally position each tube in the analysis station merely by the rotation of the carousel with no further operative steps. Positional variations of the test tube, either due to its position in the carousel or it passage into the analysis station of the detector assembly, are handled by the body member of the present invention. Moreover, the body member readily facilitates the use of round sample carriers, such as tubes or cups, which are conveniently available for laboratory procedures and uses.

Another noteworthy advantage of the detector assembly of the present invention is the ability to perform photon counting as the basis of light analysis of the sample. The desirable feature of photon counting is that it eliminates most of the noise that otherwise would be obtained with an analog signal.

DETAILED DESCRIPTION

Figure 1:
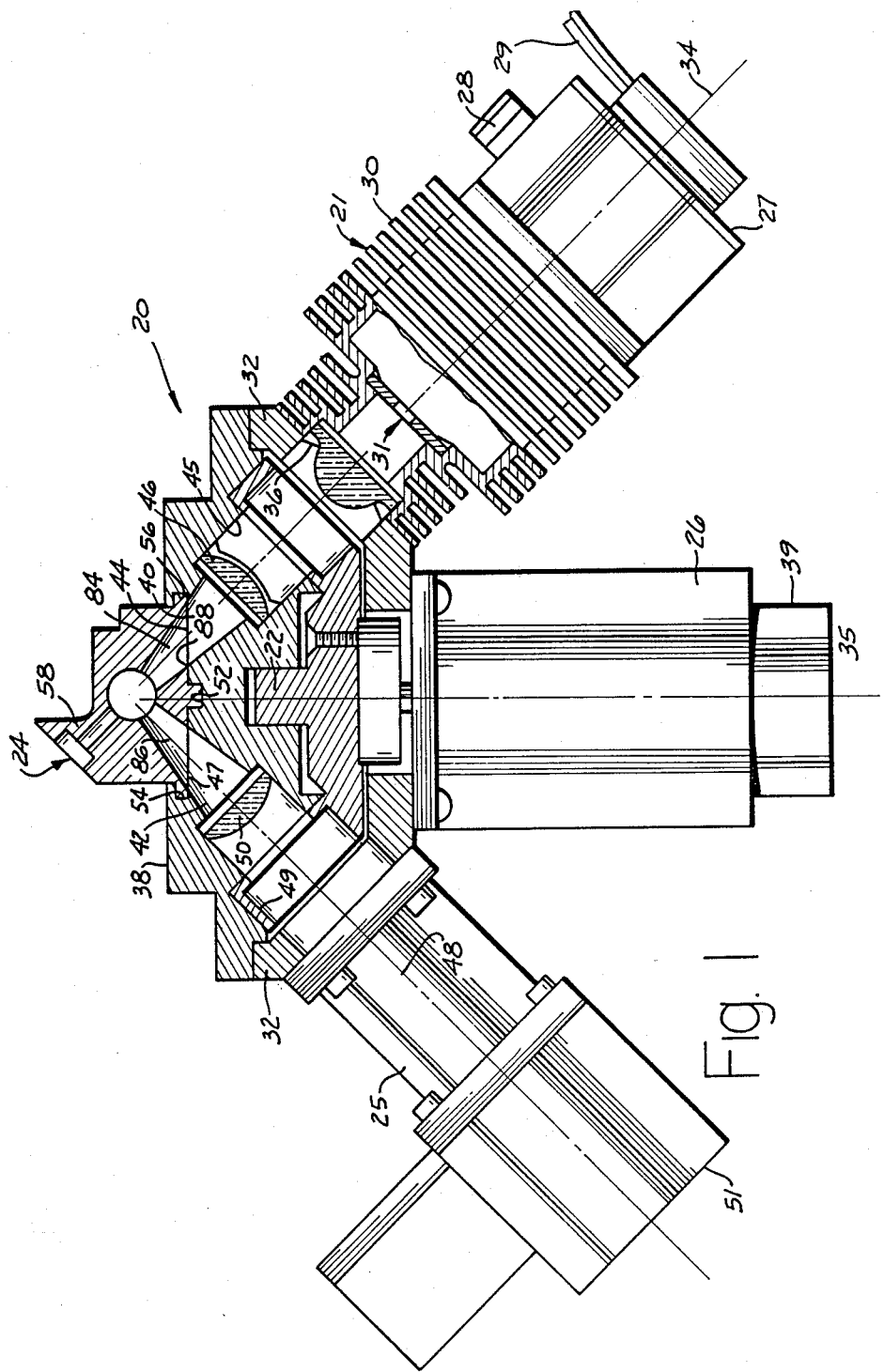
FIG. 1 is a top plan view, shown in partial section, of the preferred embodiment of the detector assembly of the present invention.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and there equivalents.

Adverting now to the drawings, and FIG. 1 in particular, there is illustrated the preferred detector assembly 20 of the present invention. Detector assembly 20 is comprised of a number of major components for purposes of fulfilling the present invention. These major components include a lamp subassembly 21, a filter wheel subassembly 22, an analysis station 24, a detector subassembly 25 and a filter wheel motor subassembly 26.

Turning first to lamp subassembly 21, it includes a housing 28 for a light source 27 which is preferably a lamp, such as a tungsten lamp. Of course the selection of light sources is a matter of choice with the equipment designer and depends upon the intended use of the analyzer, as well as the range of wavelengths that the analyzer is expected to utilize. A power cable 29 is provided as an electrical source for operating the lamp. A finned housing 30 is also associated with the lamp to facilitate the dissipation of heat generated by the lamp. A field stop 31 with a small aperture therethrough is located in the path of the light beam generated by the lamp and is positioned near the end of housing 30. It can be seen that lamp subassembly 21 is connected to detector assembly 20 by means of a detector housing 32 which is interposed between lamp subassembly 21 and filter wheel subassembly 22. Although not a requirement for the present invention, lamp subassembly 21 is connected to detector housing 32 so that its axis 34 is at an angle with respect to the axis 35 running through motor subassembly 26 and the center of analysis station 24. In the embodiment being described, the angle between axes 34 and 35 is preferably and approximately 45°.

At the interface between the connection of lamp subassembly 21 and detector housing 32 is an aspheric lens 36 which is preferably included to collimate the light from the lamp as it passes through field stop 31.

Before explaining the details of filter wheel subassembly 22, it is first appropriate to point out the details of the structure for mounting both the filter wheel subassembly and the analysis station in the present detector assembly. It can be seen in FIG. 1 that filter wheel subassembly 22 is sandwiched between detector housing 32 and a faceplate 38. Although positioned in this sandwich configuration, there is sufficient clearance between the detector housing and the faceplate for filter wheel subassembly 22 to rotate as will be explained in greater detail hereinafter. Attached to one side of detector housing 32 is filter wheel motor subassembly 26. Motor subassembly 26 includes a motor 39 which is connected by a drive shaft (not shown) through detector housing 32 and connected to filter wheel subassembly 22. Motor 39 may be controlled by appropriate electrical circuitry, including microprocessor controls, so that rotation of the filter wheel subassembly may be performed automatically and on a programmed basis, if desired.

It can be seen in the drawings that faceplate 38 is provided with two tapered passageways 40 and 42. Tapered passageway 40 extends along axis 34, aligned with lamp subassembly 21, and is therefore angularly positioned with respect to axis 35. Passageway 40 terminates in an opening 44 in the front face of faceplate 38. On the interior side of passageway 40 is a larger counterbore 45 into which is positioned a lens 46 for focusing the light beam from the lamp onto the test sample which is positioned in analysis station 24.

Passageway 42 is essentially a mirror image of passageway 40 within faceplate 38. With respect to passageway 42, it is aligned along an axis 48 which extends through detector subassembly 25 and the center of analysis station 24. Axis 48 forms an angle with respect to axis 35, and for purposes of the present invention is preferably and approximately 45°. Thus, the included angle between axes 34 and 48 is substantially at or near 90°. Tapered passageway 42 terminates in an opening 47 at the front end of faceplate 38. On the interior side of passageway 42 is a larger counterbore 49 into which a lens 50 is positioned. Lens 50 facilitates the collimation of light which emanates from the test sample within analysis station 24 so that this light may be passed into detector subassembly 25. Although not shown in the drawings, one or more lenses may be associated with detector subassembly 25 so that an efficient signal may be received therein. Detector subassembly 25 may include a photomultiplier tube 51 or other well-known devices which are designed to receive a light signal and convert it into an electrical signal.

Figure 2:
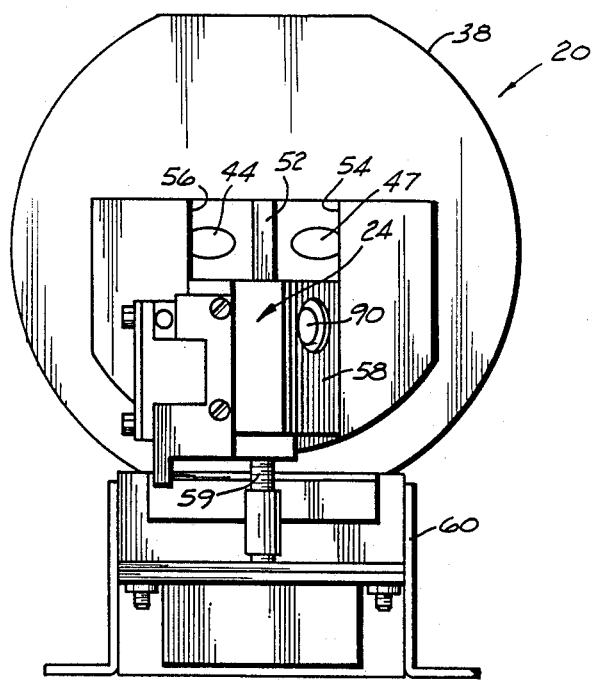
FIG. 2 is a front elevational view of the detector assembly of FIG. 1 illustrating the faceplate arrangement associated with the filter wheel and the body member for holding the sample tube in position.

On the front face of faceplate 38 there are three grooves 52, 54 and 56. Groove 52 is substantially centrally located and is preferably aligned perpendicular to axis 35; grooves 54 and 56 are laterally positioned within faceplate 38 and are opposed from each other. It is the purpose of these three grooves to facilitate the sliding movement of the analysis station represented by body member 58. Specifically, and with reference to FIG. 2, it can be seen that body member 58 is in position on faceplate 38 so that openings 44 and 47 are exposed; this position of body member 58 is consistent with the representation of the detector assembly illustrated in FIG. 6, the details of which will hereinafter be described. FIG. 2, however, illustrates that body member 58 is slidably mounted to faceplate 38 in conjunction with grooves 52, 54 and 56. For controlling sliding movement of body member 58, a shaft 59 is connected to the underside of body member 58. This shaft is associated with a servomechanism (not shown) which is appropriately controlled to move upwards or downwards, as seen in FIG. 2, for controlled movement of body member 58. This controlled movement of the body member will be discussed more fully hereinafter with respect to FIGS. 6 and 7. Other mechanisms may be used to control the sliding movement of the body member. FIG. 2 further illustrates that detector assembly 20 is supported in part by a bracket 60 which permits the mounting of the detector assembly into the analyzer instrument.

Figure 3:
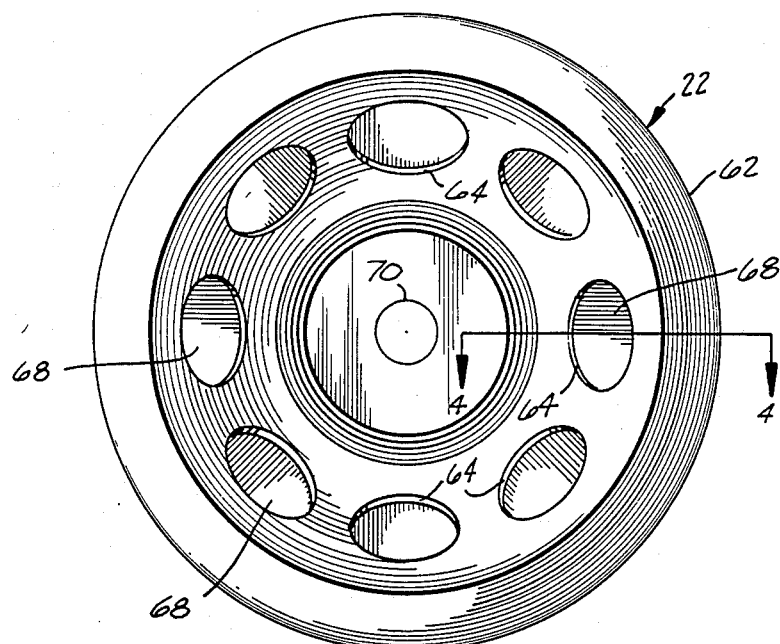
FIG. 3 is a plan view of the preferred filter wheel for the detector assembly of the present invention.
Figure 4:
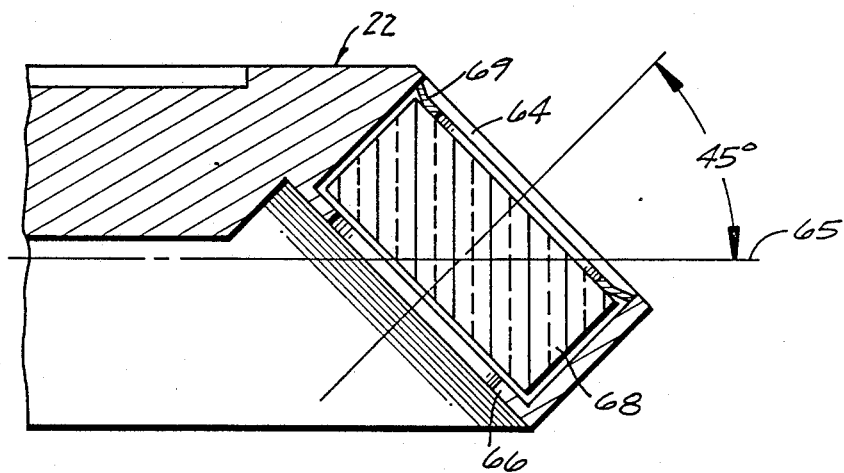
FIG. 4 is an enlarged, partial cross-sectional view of the filter wheel, taken along line 4—4 of FIG. 3.

Referring now to FIGS. 3 and 4, the details of filter wheel subassembly 22 are illustrated. Filter wheel subassembly 22 includes a filter wheel 62 generally in the shape of a substantially planar, circular disk. Around the outside periphery of wheel 62 and spaced slightly inwardly from the outer circumference, is a plurality of holes 64 extending through the wheel. In the embodiment being described, there are eight holes, although this is merely exemplary and is not construed to be limitative of the present invention. Holes 64 are oriented at an angle with respect to the plane of rotation of wheel 62, such plane of rotation designated by reference numeral 65 in FIG. 4. So that holes 64 may be aligned with the light beam travelling along axis 34 of the lamp subassembly, and similarly oriented with light emanating from analysis station 24 travelling along axis 48 toward detector subassembly 25, the angular arrangement of holes 64 is preferably and substantially at 45° with respect to the plane of rotation of wheel 62. This orientation is illustrated most clearly in FIG. 4.

Each hole 64 is preferably formed with a shoulder 66 on the faceplate side of wheel 62. One or more light filters 68 are preferably positioned in each hole 64, these filters preferably being interference filters of the type which permits the transmission of selective wavelengths of light while blocking the transmission of other wavelengths. In addition to such interference filters, any one or more holes may include a neutral density filter whose primary purpose is to attenuate ambient light to improve the signal to noise ratio of the light signal. Filters 68 may be held in position within hole 64 by virtue of a retaining or locking ring 69. Locking ring 69 may be threadably or frictionally engaged to the filter wheel so that it may be removed by the user. By removing the locking ring, the filters may be removed or interchanged by the user without the need to remove the filter wheel itself from the detector assembly. Accordingly, the configuration of the filter wheel subassembly provides sufficient flexibility for use of a plurality of different types of filters as well as selective wavelengths of transmission permitted by the filters.

As seen in FIGS. 3 and 4, holes 64 are arranged in aligned and opposed pairs so that each hole of a pair is 180° apart along the axis of rotation of the wheel. However, since each hole is oriented at an angle of 45° with respect to the plane of rotation of the wheel, it can be seen that the included angle between the holes, and between the faces of the filters within the holes, is substantially at 90°. With this arrangement of the filters within holes 64, it can be seen by referring to FIG. 1, in conjunction with FIGS. 3 and 4, that a pair of filters may be employed for each analysis of the test sample in the analysis station.

Specifically, and if, for example, the measurement to be relied upon for sample analysis is fluorescence, one filter of the pair would be selectively positioned by rotation of wheel 62 so that it is in the light beam extending along axis 34, otherwise referred to as the incident beam from the lamp. This filter permits selective wavelength transmission therethrough at a wavelength for excitation of the fluorochrome associated with the test sample. At the same time, the second filter of the pair is positioned along light axis 48 so that light emitted from the fluorochrome in the test sample may travel along that axis. This filter aligned with axis 48 may have a different characteristic of wavelength transmission so that the emitted wavelength from the fluorochrome may pass through the filter for ultimate detection in the photomultiplier tube. Accordingly, if 90° light detection is the measurement to be undertaken with the present detector assembly, it can be seen that the filter wheel of FIG. 3 permits up to four pairs of filter arrangements for each selective wavelength analysis of the test sample, whether the measurement be fluorescence, colorimetric or other light analysis. Indeed, incremental analysis of a single sample in the analysis station may be conducted with the present detector assembly merely by rotating the filter wheel. In particular, fluorescence measurements may be taken incrementally with each pair of filters employed for the fluorescence analysis. Information with respect to the fluorescence measurements may be stored, displayed or passed on for further analysis. Various ratios of light signals, particularly the emitted signals, may be established by utilizing the various measurements afforded by the selective wavelength analysis of the singular test sample.

Further, one or more of holes 64 may include a filter which may be used for reference purposes so that a standard basis of signal measurement may be established either in absolute terms or by utilizing a ratio of signals, one of which is based on the reference filter. Although the embodiment illustrated in FIG. 1 is arranged so that the incident light beam and the detected light beam (associated with a signal from the test sample) are at 90° with respect to each other, such angular orientation is merely the preferred embodiment of the invention. As will be pointed out hereinafter with respect to the discussion of the details of body member 58, the axis of the light detector may vary, if so desired. For instance, the light detector may be positioned at an angle approximately 180° with respect to the axis of incident light from the lamp represented by axis 34 in FIG. 1. If the light detector is at such a 180° orientation, light absorbance may be the measurement undertaken. Also, at angles near 180°, the light detector may measure forward light scatter from the incident light beam. Other angular orientations, both narrow and wide, may be chosen for the position of the light detector with respect to the axis of the incident light beam.

Before leaving FIGS. 3 and 4, it should be pointed out that wheel 62 includes a central bore 70 into which the shaft (not shown) of drive motor 39 is positioned. The connection between this shaft and filter wheel 62 provides the mechanism so that wheel 62 may be rotated by motor 39 preferably in a controlled, automatic fashion, either on a pre-programmed basis or command by the user.

Figure 5:
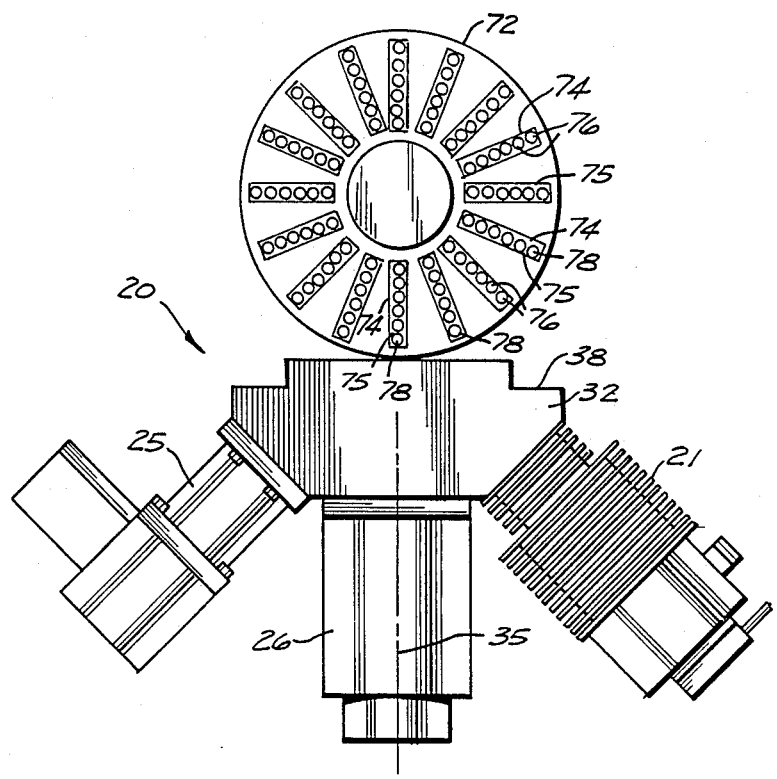
FIG. 5 is a top plan view of the detector assembly of the present invention shown in juxtaposition with a carousel for holding a plurality of test sample packages.

Reference is now made to FIG. 5 which illustrates detector assembly 20 as it may appear in an analyzer instrument of the type which includes a carousel 72 for holding test samples for analysis. A particular analyzer instrument, including a carousel arrangement, for which the detector assembly hereof is eminently suited is described in commonly assigned and co-pending patent application Ser. No. 799,238, filed on Nov. 18, 1985. Carousel 72 is substantially similar to the carousel described in the aforementioned patent application. As seen in FIG. 5, carousel 72 includes a plurality of radially extending slots 74. Into each slot is positioned a reagent package 75, in this embodiment containing a plurality of receptacles or wells 76. As explained in the aforementioned patent application, the different wells in reagent package 75 may include pre-packaged reagents and may be used for mixing purposes, except for the well 78 at the end of the reagent package facing the periphery of carousel 72. Such a reagent package is described in U.S. Pat. No. 4,608,231. Well 78 of each reagent package is intended to be the carrier for the sample to be analyzed and through which the light beam is to pass so that the liquid sample may undergo light analysis. Carousel 72 is a rotatable device which incrementally turns so that each reagent package may pass in front of the detector assembly, and in particular, each well 78 pass into the analysis station of the detector assembly.

Figure 6:
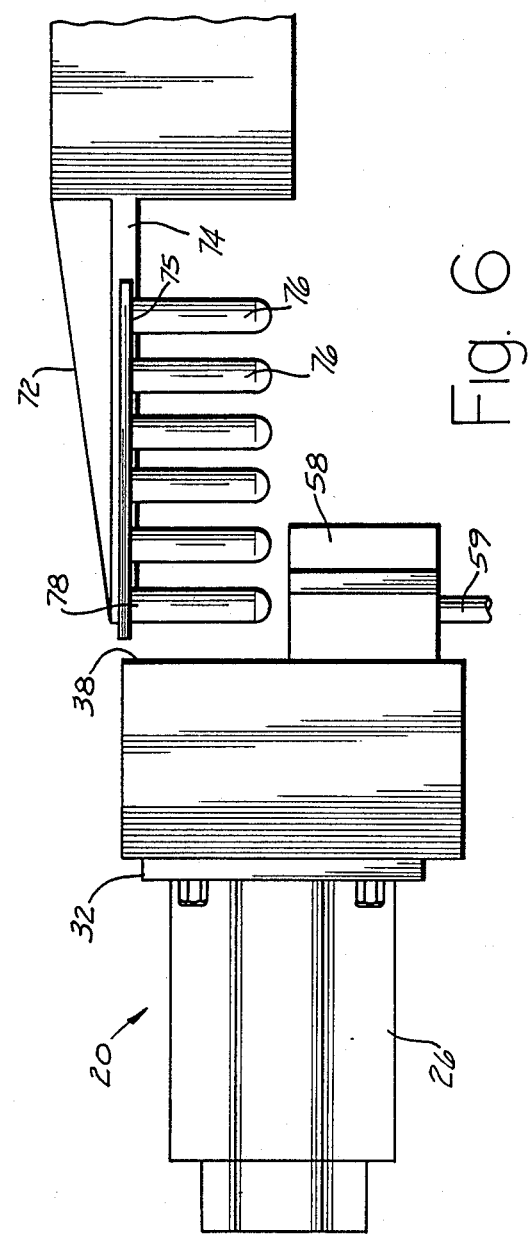
FIG. 6 is a side elevational view of the detector assembly illustrating the movement of the body member away from the tube carrying the sample for analysis so that the carousel may turn for incrementally positioning different sample packages into the detector assembly.
Figure 7:
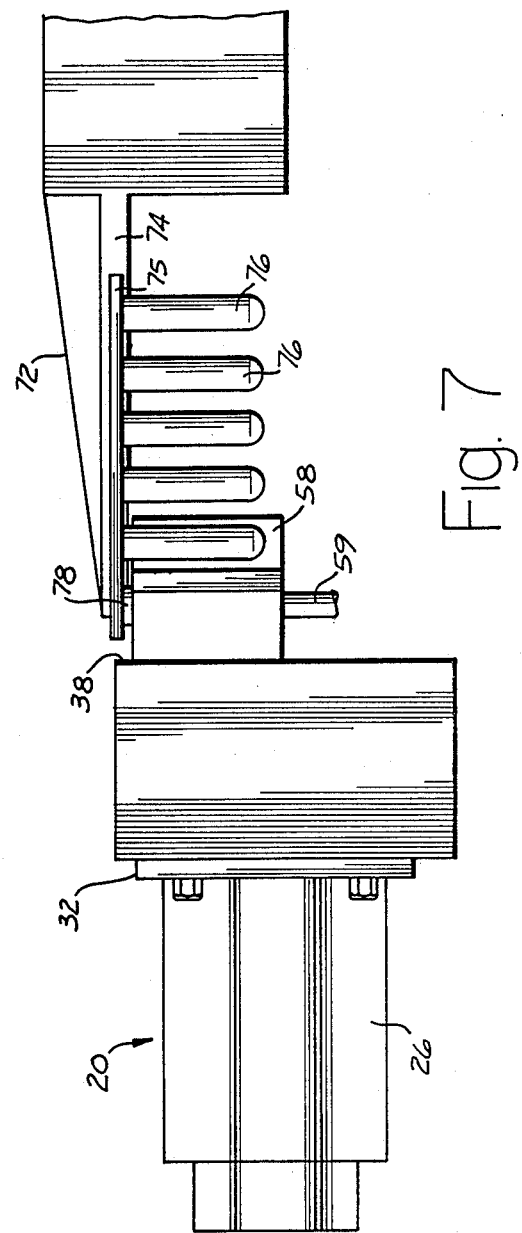
FIG. 7 is a side elevational view similar to FIG. 6 illustrating one tube of the sample package positioned in the body member for sample analysis while the sample package is in position on the carousel.

It is understood that while FIG. 5 illustrates, along with the present description, the utilization of a reagent package with a plurality of receptacles or wells, other analyzer instruments may handle the sample carrying receptacles on an individualized basis, each of which may be moved into and out of the analysis station of the instant detector assembly. It can be seen in FIG. 5 that the reagent package which includes the test sample for analysis is aligned along axis 35 of detector assembly 20. When slot 74 with reagent package 75 is at this location, carousel 72 is designed to stop its rotation so that the test sample in well 78 may undergo light analysis. FIGS. 6 and 7 illustrate the operative details of the analysis station of the detector assembly, with particular emphasis on the operation of body member 58.

Viewing FIG. 6 first, it can be seen that carousel 72 has carried reagent package 75 in front of detector assembly 20 so that well 78 is in close juxtaposition to faceplate 38. In the configuration of FIG. 6, body member 58 is at the lower or downward position controlled by the movement of shaft 59. Accordingly, carousel 72 is free to rotate whereby reagent package 75, with depending wells 76 and 78, passes over body member 58. When a reagent package is aligned along axis 35 (as explained with respect to FIG. 5), carousel 72 stops its rotation, and shaft 59 is caused by the appropriate servomechanism to move upwards, thereby sliding body member 58 in the same direction. This upward movement of the body member results in the capturing of well 78 within the body member, so that the body member provides both a light shielding and position maintaining effect. FIG. 7 illustrates the position of body member 58 with respect to the well 78. Light may now be directed into well 78 so that the sample therein may be tested and analyzed for chemical, immunochemical or biological substances or effects in known fashion. When the sample analysis is complete, body member 58 may move downwards again, either on a programmed basis or upon command of the user, so that the carousel may rotate to incrementally move the next reagent package before the detector assembly.

Figure 8:
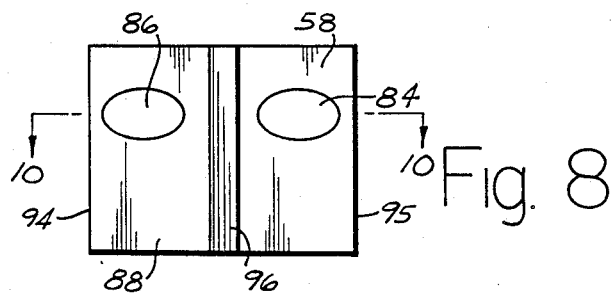
FIG. 8 is a front elevation view of the preferred embodiment of the body member of the present invention.
Figure 9:
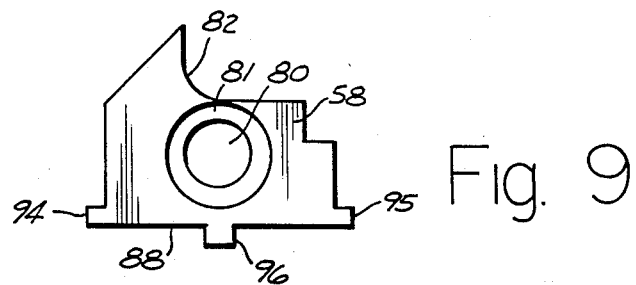
FIG. 9 is a top plan view of the body member of FIG. 8.
Figure 10:
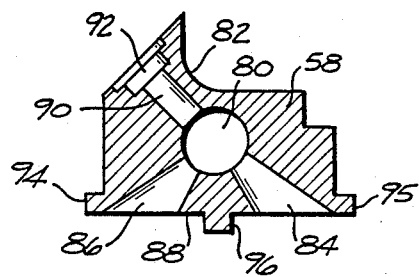
FIG. 10 is a cross-sectional view of the body member taken along line 10—10 of FIG. 8.

FIGS. 8–10 illustrate the details of body member 58. This body member, as part of the analysis station, is intended to be a multi-purpose element. In addition to being a light shield so that the test sample may be shielded from extraneous light, this body member serves as a guide for holding in position the carrier for the test sample. Insofar as many carriers for these tests samples are conveniently round tubes, such as test tubes, the body member of the present invention serves as a desirable element to handle round tubes without incurring positional variations with respect to the light beam. To that end, body member 58 preferably includes a substantially cylindrical bore 80 extending in a direction for receipt of a rounded tube, such as well 78 of the reagent package described above. Surrounding the top surface of bore 80 is a countersink or chamfer 81 which facilitates the relative sliding movement between the body member and the tube so that locational differences of different tubes may be accounted for. When body member 58 is in the upward position, such as seen in FIG. 7, tube 78 is positioned within bore 80 so that the body member surrounds the tube. It is preferred that body member 58 be finished with a black coating or painting so that the light shielding features of the body member may be maximized. So that a reagent package with a plurality of wells or tubes, such as package 75 described above, may be utilized with the present detector assembly without the need for removing the test well from the package, a cut-out portion 82 of the body member is provided. It is understood that this cut-out portion is merely a preferable embodiment since the configuration of the body member may be designed to accommodate a variety of tubes or wells for carrying the sample to be analyzed.

Communicating with bore 80 are two apertures 84 and 86. These apertures are preferably tapered so that they narrow as the aperture approaches bore 80. Each aperture 84 and 86 is positioned on an axis which is substantially at 45° with respect to the plane of face 88 of the body member. Face 88 is intended to mate in sliding engagement with the front face of face plate 38. Further, the orientation of apertures 84 and 86 into the body member is consistent with the 45° angular position of axis 34 for the incident light beam and with axis 48 for the detected light. The included angle between the axes of apertures 84 and 86 is thus substantially and preferably at 90°.

When body member 58 is in the upward position, as illustrated in FIG. 7, apertures 84 and 86 are in alignment with openings 44 and 47, respectively, in faceplate 38. Alignment of the respective apertures and openings permits the incident light beam to pass through aperture 84 and also through the light transmissive tube carrying the test sample so that the sample may be analyzed. Light emanating from the sample is detected at a 90° angle along axis 48 by virtue of the alignment of opening 47 and aperture 86, as illustrated in FIG. 1.

Body member 58 has additional versatility with respect to the detection of light from the test sample within bore 80. To this end, a third aperture 90 extends through the body member in communication with bore 80. Aperture 90 is preferably oriented along the same axis as the axis of aperture 84 so that aperture 84 and aperture 90 are substantially 180° apart. A larger counterbore 92 may be provided with respect to aperture 90 for the inclusion of optical elements such as filters, lenses or even light barriers, such as plugs, in order to prevent light from passing through aperture 90. If aperture 90 is to be utilized in conjunction with the present detector assembly, it would be desirably suitable for detecting forward light scatter, absorbance measurements and the like. In using aperture 90 to detect light from the test sample, the light detector may be positioned on the same 180° axis with respect to the incident beam of light, or the light detector may be positioned on a different angle and light directed to it by use of one or more mirrors or prisms.

Body member 58 is slidably connected to faceplate 38 so that face 88 of the body member is in face-to-face engagement. To facilitate this slidable connection, body member 58 includes two lateral flanges 94 and 95 which are sized to slidably fit wirhin lateral grooves 54 and 56, respectively, in faceplate 38. A guide bar 96 protrudes from face 88 and is substantially centrally located thereon. This guide bar is slidably insertable into groove 52 centrally positioned in faceplate 38 along axis 35. Thus, the lateral flanges and the guide bar of body member 58 permit the body member to slidably move with respect to the faceplate. As described above, shaft 59, which may be threaded into a threaded portion provided at the bottom of bore 80, is provided to control the movement of the body member both upwardly and downwardly, although other mechanics may be employed in accordance with this invention.

One of the advantages attributed to the present invention is the ability to employ a light detector which counts photons of light issuing from the test sample under analysis. One of the holes in filter wheel 62 may include, either in addition to or alternatively for the interference filter, a neutral density filter, as was previously mentioned. If such a neutral density filter is employed in the filter wheel, it would be included as one filter in a particular pair of filters so that the neutral density filter would be interposed in the light path between the test sample and the light detector along axis 48. Another neutral density filter may be included along light axis 48 just prior to photomultiplier tube 51. These neutral density filters desirably keep the ratio of light excitation to ambient light at a very high level. As a result, although a small percentage of light is ultimately passed to the light detector, substantially all ambient light is attenuated. With the neutral density filters eliminating substantially all background noise (light) photon counting may be achieved. Photon counting eliminates all but about 0.1% of the noise that otherwise would be obtained with the detection of an analog signal. Furthermore, a wide dynamic range results from using photon counting, up to a ratio of about 2000:1. In addition, insofar as photon counting provides a direct digital measurement of the light signal that is relatively stable, it frees the user from making those kind of signal adjustments that are attendant to analog signals.

Thus, the present invention provides a detector assembly which is suitable for use in an analyzer instrument, particularly such instruments which detect light associated with tests for chemical, immunochemical or biological substances or effects. The present invention is eminently suitable for use with round tubes or carriers into which the sample for analysis is placed. Positional variations in the tubes which carry the sample are managed quite well by the present detector assembly so that inaccuracies due to positional effects are minimized and reduced. Furthermore, the present detector assembly provides for multiple and selective wavelength analysis of the test sample without the need for changing light filters or the like during the analysis of the test sample. As a result of the present invention, the operation, efficiency and performance of the analyzer instrument are improved.

What is claimed is:

1. A detector assembly suitable for use in an instrument for analyzing samples carried in a light transmissive carrier comprising:
   a light source for providing a light beam for use in analyzing one or more substances in a sample;
   a detector for detecting light associated with the sample under analysis;
   an analysis station into which a carrier for the sample to be analyzed is positionable and into which the light beam is to be directed, said analysis station including a body member with a central opening for receiving the carrier and for surrounding same to shield the sample from extraneous light and to maintain the position of the carrier during analysis, said station including a first aperture in communication with said central opening for permitting incident light from the beam to enter the carrier with the sample, and a second aperture in communication with said central opening for permitting light to pass from the sample to said detector so that the sample may be analyzed;
   a coating on said body member around the central opening to maximize the light shielding of the sample from extraneous light; and
   a rotatable filter wheel having a plurality of light filters spaced in a substantially circular arrangement in said wheel, each filter being interposable in the light beam between the light source and the analysis station, the filters permitting different wavelengths of light to pass therethrough so that selective light analysis of the sample may be performed depending upon the position of the wheel.

2. The assembly of claim 1 which further includes a first lens for focusing the light beam from said source into the analysis station.

3. The assembly of claim 2 which further includes a second lens for focusing the light from the sample into the detector.

4. The assembly of claim 1 wherein said central opening is a substantially cylindrical bore for surrounding a substantially cylindrical carrier which carries the sample for analysis.

5. The assembly of claim 4 wherein said body member is movable between a first position at which the central opening surrounds the carrier and a second position out of surrounding association with said carrier to facilitate the passage of the carrier into and out of said analysis station.

6. The assembly of claim 5 which further includes means for operatively moving said body member between the first and second positions to accommodate the receipt of the carrier into the analysis station.

7. The assembly of claim 1 wherein the included angle between the first and second apertures is substantially 180°.

8. The assembly of claim 1 wherein the included angle between the first and second apertures is substantially 90°.

9. The assembly of claim 8 which further includes a third aperture in communication with said central opening for permitting light to pass from said sample to said detector, wherein the included angle between the first and third apertures is substantially 180°.

10. The assembly of claim 1 wherein said filters are removably positioned in said wheel so that the filters may be removed without dissembling the wheel from the assembly.

11. The assembly of claim 1 which further includes means for rotating said wheel so that the filters are selectively positionable in the light beam between said light source and said analysis station.

12. The assembly of claim 1 wherein each filter is positioned in said wheel at an angle substantially at 45° with respect to the plane of rotation of said wheel.

13. The assembly of claim 12 wherein the filters are arranged in aligned and opposed pairs so that the included angle between the faces of each pair of filters is substantially 90°.

14. The assembly of claim 13 wherein one filter of each pair is interposed in the light beam between the light source and the analysis station and the other filter of each pair is interposed in the light path between the sample and the detector.

15. The assembly of claim 14 wherein each pair of filters is selected so that the first filter of the pair passes light at a wavelength to excite a fluorochrome associated with the sample under analysis and the second filter of the pair passes light at a wavelength of emission from said fluorochrome.

16. The assembly of claim 1 wherein said detector is selected to receive fluorescent emissions from said sample.

17. The assembly of claim 1 wherein said detector is selected to count photons emitted from said sample.

18. The assembly of claim 1 wherein said detector is selected to receive light scattered by said sample.

19. The assembly of claim 1 wherein said detector is selected to measure light absorbed by said sample.

20. A detector assembly for use with an analyzer instrument comprising:
   means for providing a light beam for analyzing one or more substances in a sample;
   means for detecting light associated with said sample under analysis;
   means for permitting said light beam to enter said sample and for shielding said sample from extraneous light and for maintaining the position of the sample during analysis, said permitting means further permitting light to pass from said sample to said means for detecting;
   a coating on a surface associated with said permitting and shielding means to maximize the light shielding of the sample from extraneous light; and
   a plurality of filters selectively positionable in the light beam between the means for providing light and the sample, the filters permitting different wavelengths of light to pass therethrough so that selective light analysis of the sample may be performed.

21. A detector assembly for use in an instrument for analyzing samples carried in a light transmissive tube comprising:
   a light source for providing an incident light beam for use in analyzing one or more substances in a sample;
   a detector for detecting light associated with the sample under analysis;
   an analysis station including a movable body member with a substantially cylindrical bore into which a tube carrying the sample to be analyzed is positionable, said body member surrounding the tube when positioned in the bore to shield the sample from extraneous light to maintain the position of the tube during analysis, said body member including a first aperture in communication with said bore for permitting incident light to enter the tube with the sample and a second aperture in communication with said bore for permitting light to pass from said sample to said detector so that the sample may be analyzed, said body member being operatively movable between a first position at which the bore surrounds the tube and a second position out of surrounding association with the tube to facilitate the passage of the tube into and out of the analysis station;

a coating on said body member around the central opening to maximize the light shielding of the sample from extraneous light;

a rotatable filter wheel having a plurality of removably mounted light filters spaced in a substantially circular arrangement in said wheel, each filter being interposable in the light beam between the light source and the analysis station, the filters permitting different wavelengths of light to pass therethrough so that selective light analysis of the sample may be performed depending upon the position of the filter wheel; and means for rotating said wheel so that each filter is selectively positionable in the light beam between the light source and the analysis station.

* * * * *